(12) United States Patent
Ganley et al.

(10) Patent No.: US 7,894,769 B2
(45) Date of Patent: Feb. 22, 2011

(54) WIRELESS MICROPHONE COMMUNICATION SYSTEM

(75) Inventors: Richard Ganley, Morden (GB); Tomohisa Tanaka, Hyogo (JP)

(73) Assignees: Toa Corporation, Kobe-shi (JP); BBM Electronics Group Limited, Morden, Surrey (GB)

( * ) Notice: Subject to any disclaimer, the term of this patent is extended or adjusted under 35 U.S.C. 154(b) by 158 days.

(21) Appl. No.: 10/564,255

(22) PCT Filed: Jul. 12, 2004

(86) PCT No.: PCT/JP2004/010255
§ 371 (c)(1),
(2), (4) Date: Sep. 21, 2006

(87) PCT Pub. No.: WO2005/006806
PCT Pub. Date: Jan. 20, 2005

(65) Prior Publication Data
US 2007/0113727 A1    May 24, 2007

(30) Foreign Application Priority Data

Jul. 10, 2003    (JP) .............................. 2003-272876

(51) Int. Cl.
*H04B 7/24* (2006.01)
*H04M 3/42* (2006.01)
*H04B 7/00* (2006.01)
*H04R 3/00* (2006.01)

(52) U.S. Cl. .................. 455/39; 455/416; 455/66.1; 381/122

(58) Field of Classification Search .............. 381/122, 381/92, 56, 77, 95, 111; 455/416, 39, 66.1; 370/260
See application file for complete search history.

(56) References Cited

U.S. PATENT DOCUMENTS 4,882,773 A    11/1989    Maloney (Continued)

FOREIGN PATENT DOCUMENTS

EP    0730388    9/1996

(Continued)

OTHER PUBLICATIONS

International Search Report (ISR) for International Application No. PCT/JP2004/010255 by Japanese Patent Office dated Oct. 21, 2004 (1 page).

(Continued)

*Primary Examiner*—Vivian Chin
*Assistant Examiner*—George Monikang
(74) *Attorney, Agent, or Firm*—Marshall, Gerstein & Borun LLP

(57) ABSTRACT

A wireless microphone communication system 1 comprises one or more controllers 21 to 24 having LAN interfaces, one or more receivers 11 to 18 having the LAN interfaces and being configured to receive a radio wave from a transmitter of a wireless microphone. The one or more receivers 11 to 18 are coupled to the one or more controllers 21 to 24 on LAN. Each controller 21 to 24 is coupled to a corresponding display device. Each controller 21 to 24 receives, from the one or more receivers 11 to 18, information of the receiver through the LAN. Each controller 21 to 24 causes the received information of the receiver to be displayed on the corresponding display device.

6 Claims, 7 Drawing Sheets

U.S. PATENT DOCUMENTS

| | | | |
|---|---|---|---|
| 5,003,532 A * | 3/1991 | Ashida et al. ............. 348/14.09 |
| 5,072,442 A * | 12/1991 | Todd ........................... 370/265 |
| 5,832,390 A | 11/1998 | Irvin |
| 5,943,649 A * | 8/1999 | Fado et al. .................. 704/270 |
| 6,038,429 A | 3/2000 | Ahn |
| 6,057,758 A | 5/2000 | Dempsey et al. |
| 6,246,325 B1 | 6/2001 | Chittipeddi |
| 6,317,039 B1 | 11/2001 | Thomason |
| 6,667,764 B1 | 12/2003 | Wakiyama et al. |
| 6,987,949 B2 | 1/2006 | Taniguchi et al. |
| 7,054,625 B2 * | 5/2006 | Kawasaki et al. ............ 455/420 |
| 2002/0005894 A1 | 1/2002 | Foodman et al. |
| 2002/0042282 A1 | 4/2002 | Haupt |
| 2002/0129379 A1 * | 9/2002 | Levinson et al. ............. 725/129 |
| 2003/0220123 A1 * | 11/2003 | Motohashi ................ 455/550.1 |
| 2004/0121819 A1 | 6/2004 | Vogel |

FOREIGN PATENT DOCUMENTS

| | | |
|---|---|---|
| EP | 1197178 | 4/2002 |
| EP | 1 309 222 A2 | 5/2003 |
| JP | 61-105997 | 5/1986 |
| JP | 05-183788 A | 7/1993 |
| JP | 05-68193 A | 9/1993 |
| JP | 10-070472 A | 3/1998 |
| JP | 10124790 | 5/1998 |
| JP | 2001-045116 A | 2/2001 |
| JP | 2001-144645 A | 5/2001 |
| JP | 2002-009708 A | 1/2002 |
| JP | 2002-156985 A | 5/2002 |
| JP | 2003-102074 | 4/2003 |
| JP | 2003-174382 A | 6/2003 |

OTHER PUBLICATIONS

Supplementary Partial European Search Report for European Application No. EP 04747719, dated Mar. 4, 2009.
Communication for European Application No. EP 04747720.3, dated Sep. 21, 2009.
International Search Report for Application No. PCT/JP2004/010256, dated Oct. 14, 2004.
Notification of Reasons for Refusal.
Supplementary Partial European Search Report for Application No. PCT/JP2004/010256, dated Apr. 14, 2009.
Response to Restriction Requirement for U.S. Appl. No. 10/564,213, filed by Applicant on Dec. 8, 2009.
Restriction Requirement for U.S. Appl. No. 10/564,213, issued by Patent Office on Nov. 12, 2009.
Final Office Action for U.S. Appl. No. 10/564,213, issued by Patent Office on Apr. 27, 2009.
Amendment in Response to Non-Final Office Action for U.S. Appl. No. 10/564,213, filed by Applicant on Jan. 20, 2009.
Non-Final Office Action for U.S. Appl. No. 10/564,213, issued by Patent Office on Aug. 14, 2008.

* cited by examiner

WIRELESS MICROPHONE COMMUNICATION SYSTEM

CROSS-REFERENCE TO RELATED APPLICATION

The present application claims the benefit of priority of International Patent Application No. PCT/JP2004/010255 filed on Jul. 12, 2004, which application claims priority of Japanese Patent Application No. 2003-272876 filed Jul. 10, 2003. The entire text of the priority application is incorporated herein by reference in its entirety.

TECHNICAL FIELD

The present invention relates to a wireless microphone communication system and, particularly to a wireless microphone communication system suitable for use associated with a stage.

BACKGROUND ART

In some cases, wireless microphones are used on a stage. Plural performers who work on stage carry portable wireless microphones. Voices emitted from the performers are received by the microphones and loud sound waves are emitted from a loudspeaker installed on the stage.

A radio wave from the wireless microphone carried by each performer is sent to the corresponding receiver. The radio wave is not always received in good condition by the receiver. For instance, an operator A that monitors a procedure of performance on the stage while manipulating a mixing console may notice that the radio wave from the wireless microphone of one performer is not received in good condition by the receiver. In that case, the operator A must instruct another operator (operator B) who is on backstage to check or maintain the wireless microphone. To this end, the operator A provides an instruction to the operator B on backstage by using an intercom system or the like within that hall.

Such a method will not arise a severe problem when a communication system using wireless microphones is small-scaled and operators are few. On the other hand, a number problems will arise when a communication system using wireless microphones is large-scaled and operators are many. For example, an instruction from a main operator to another operator may become intricate, or otherwise the main operator is unable to confirm that another operator conducted as instructed by the main operator. These problems may be due to the fact that all the operators have difficulty in equally recognizing a condition of the communication system using the wireless microphones.

When the instruction is communicated from one operator to another by voice, they are unable to emit a large voice, for example, during the performance. It may be difficult to correctly determine who has provided the instruction.

When the intercom system is wireless, interference between the intercom system and the microphone system may occur.

Transmitters of wireless microphones for use on stage are in some cases embedded in, for example, clothes of performers. For each maintenance or each initial setting of the transmitters, it becomes necessary to take out the microphones from the clothes in order to operate operation portions of the transmitters of the wireless microphones. In many cases, maintenance and initial setting may be difficult.

For example, Japanese Laid-Open Patent Application Publication No. 2002-119774 discloses a wireless operating system for stage apparatuses. But, the system disclosed therein is incapable of solving the above mentioned problems.

DISCLOSURE OF THE INVENTION

Under the circumstances, the present invention has been made. An object of the present invention is to provide a wireless microphone communication system that enables plural operators to equally recognize a condition of a communication system using wireless microphones.

In order to achieve the above mentioned object, according to an aspect of the present invention, a wireless microphone communication system comprises one or more controllers having LAN interfaces; one or more receivers having the LAN interfaces and being configured to receive a radio wave from a transmitter of a wireless microphone; wherein the one or more receivers are coupled to the one or more controllers on LAN; each controller is coupled to a corresponding display device; each controller receives, from the one or more receivers, information of the receiver through the LAN; and each controller causes the received information of the receiver to be displayed on the corresponding display device.

In order to achieve the above mentioned object, according to another aspect of the present invention, a wireless microphone communication system comprises one or more controllers that have LAN interfaces and are coupled to a receiver configured to receive a radio wave from a transmitter of a wireless microphone; one or more controllers that have the LAN interfaces and are not coupled to the receiver; wherein the controllers are coupled on LAN; each controller is coupled to a corresponding display device; each controller receives, through the LAN, information of the receiver coupled to another controller from the another controller coupled to the receiver; each controller that is not coupled to the receiver causes the information of the receiver that has been received through the LAN to be displayed on the corresponding display device; and each controller that is coupled to the receiver causes the information from a corresponding receiver and the information of the receiver that has been received through the LAN to be displayed on the corresponding display device.

In order to achieve the above mentioned object, according to another aspect of the present invention, a wireless microphone communication system comprises a plurality of controllers that have LAN interfaces and are coupled to a receiver configured to receive a radio wave from a transmitter of a wireless microphone; wherein the controllers are coupled on LAN; each controller is coupled to a corresponding display device; each controller receives, through the LAN, information of the receiver coupled to another controller from the another controller coupled to the receiver; and each controller causes the information from a corresponding receiver and the information of the receiver that has been received through the LAN to be displayed on the corresponding display device.

In accordance with the above mentioned wireless microphone communication system, plural operators are able to equally recognize the condition of the communication system using wireless microphones, and to change settings of the microphones and the like quickly.

In the wireless microphone communication system, each controller may create an alarm message based on the received information of the receiver and cause the alarm message to be displayed on the corresponding display device.

In the wireless microphone communication system, each controller may be coupled to a corresponding input device; each controller may receive character string information from the corresponding input device and may send the character string information to another controller through the LAN; and each controller may cause the character string information input from the corresponding input device and the character string information from the another controller to be displayed on the corresponding display device together with the information of the receiver.

In the wireless microphone communication system, the character string information may be displayed as being associated with one information within the information of plural receivers on the display device; and the character string information may be information relating to a receiver corresponding to the one information within the information of the plural receivers.

In the wireless microphone communication system, the character string information may be displayed to have a color identical to a color of the one information within the information of the plural receivers.

In the wireless microphone communication system, the character string information may be located in the vicinity of the one information within the information of the plural receivers on the display device.

In the wireless microphone communication system, each receiver may receive a control signal from any one of the controllers and may change a setting condition according to the control signal.

In the wireless microphone communication system, the controller may be configured by a computer.

In the wireless microphone communication system, one application program running on each computer may cause the character string information input from a corresponding input device and the character string information from another computer to be displayed on one window of the corresponding display device together with the information from the receiver.

The wireless microphone communication system may further comprise a television camera; wherein the television camera may be coupled onto the LAN; and an image from the television camera may be displayed on the display device of each controller together with the information of the receiver.

In the wireless microphone communication system, at least one controller may be coupled to a storage means, and cause image information from the television camera and information based on the information of the receiver to be stored in the storage means.

The wireless microphone communication system may further comprise a television camera; and a storage means; wherein at least one controller of the controllers may receive image information from the television camera; the controller that receives the mage information continuously detects information of RF level from the receiver through LAN; and the controller that receives the image information may determine whether or not the detected RF level is not higher than a predetermined level, and when determining that the detected RF level is not higher than the predetermined level, the controller may cause the image information from the television camera to be stored in the storage means.

The wireless microphone communication system may further comprise a time measuring means; wherein the controller that receives the image information may receive time information from the time measuring means; when determining that the detected RF level is not higher than the predetermined level, the controller that receives the image information may cause the image information from the television camera to be stored in the storage means together with the time information from the time measuring means.

In the wireless microphone communication system, the controller that receives the image information may continuously detect information of the RF level from the receiver through the LAN.

These objects as well as other objects, features and advantages of the invention will become more apparent to those skilled in the art from the following description with reference to the accompanying drawings.

BEST MODE FOR CARRYING OUT THE INVENTION

Embodiments of the present invention will be described with reference to the drawings.

Figure 1:
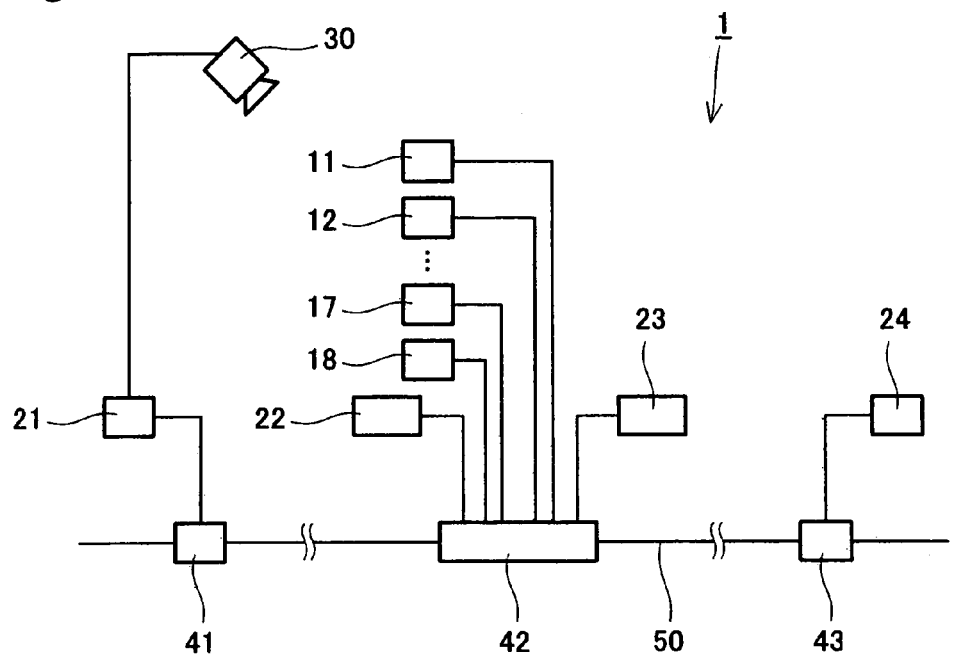
FIG. 1 is a block diagram of a wireless microphone communication system.

FIG. 1 is a block diagram of a wireless microphone communication system 1 according to an embodiment of the present invention.

The wireless microphone communication system 1 is installed for a performance on a stage.

The wireless microphone communication system in FIG. 1 comprises receivers 11, 12, . . . , 17 and 18 that respectively receive radio waves from transmitters of the wireless microphones, computers 21, 22, 23, and 24 which are control devices, and a television camera 30.

The receivers 11, 12, . . . , 17 and 18 and the computers 21, 22, 23, and 24 have LAN interfaces. The receivers 11 to 18 and the computers 21 to 24 are coupled to Ethernet 50 through HUB 41, 42, and 43, thus entirely configuring LAN.

The television camera 30 is coupled to the computer 21.

The computer 24 is installed at a position from which the computer 24 is able to observe the entire stage. At that position, there is installed a mixing console for controlling entire electric acoustic equipment (loudspeaker) for emitting a loud sound wave of the voice that is received by the wireless microphone. An operator A stands by near the computer 24.

The receivers 11 to 18 and the computer 22 are installed on a wing of the stage. An operator B stands by near the receivers 11 to 18 and the computer 22.

Figure 2:
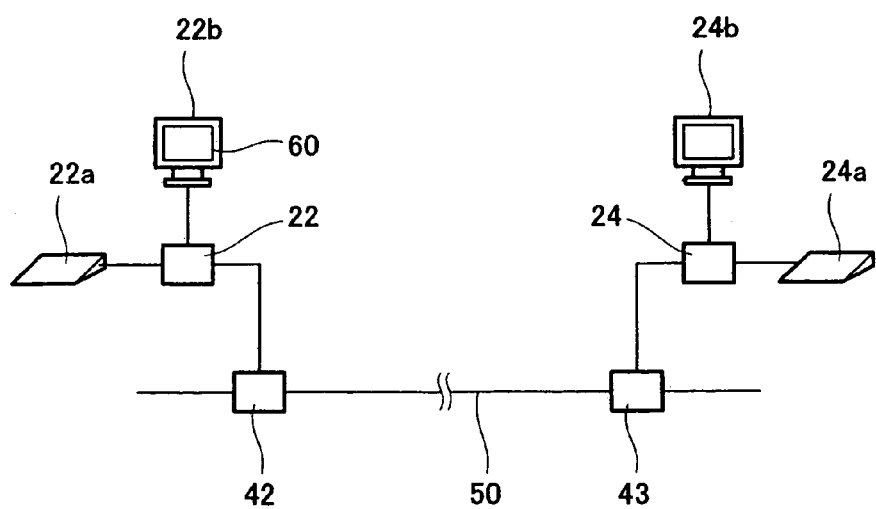
FIG. 2 is a block diagram showing computers and peripheral devices coupled to the computers.

FIG. 2 is a block diagram showing the computers 22 and 24 and peripheral devices coupled to the computers 22 and 24. Although not shown in FIG. 1, a key board 22*a* which is an input device and a display device 22*b* are coupled to the computer 22. A key board 24*a* which is an input device and a display device 24*b* are coupled to the computer 24. Although not shown in FIG. 2, key boards and display devices are coupled to the computers 21 and 23 in the same manner.

The computers 21 to 24 receive information from the receivers 11 to 18 through the LAN. The information from the receivers 11 to 18 includes an RF level (receiving field intensity), an audio output level (VU level), etc. Information indicating battery powers of the wireless microphones are output from the wireless microphones corresponding to the receivers 11 to 18, and the computers 21 to 24 receive information indicating the battery powers from the receivers 11 to 18.

An application program E to which these information are input runs on the computers 21 to 24. The same application program E runs on the computers 21 to 24.

Character string information input from the key board, as well as the information from the receivers 11 to 18, are input to the application program E. The application program E causes the corresponding display device to display one window.

Figure 3:
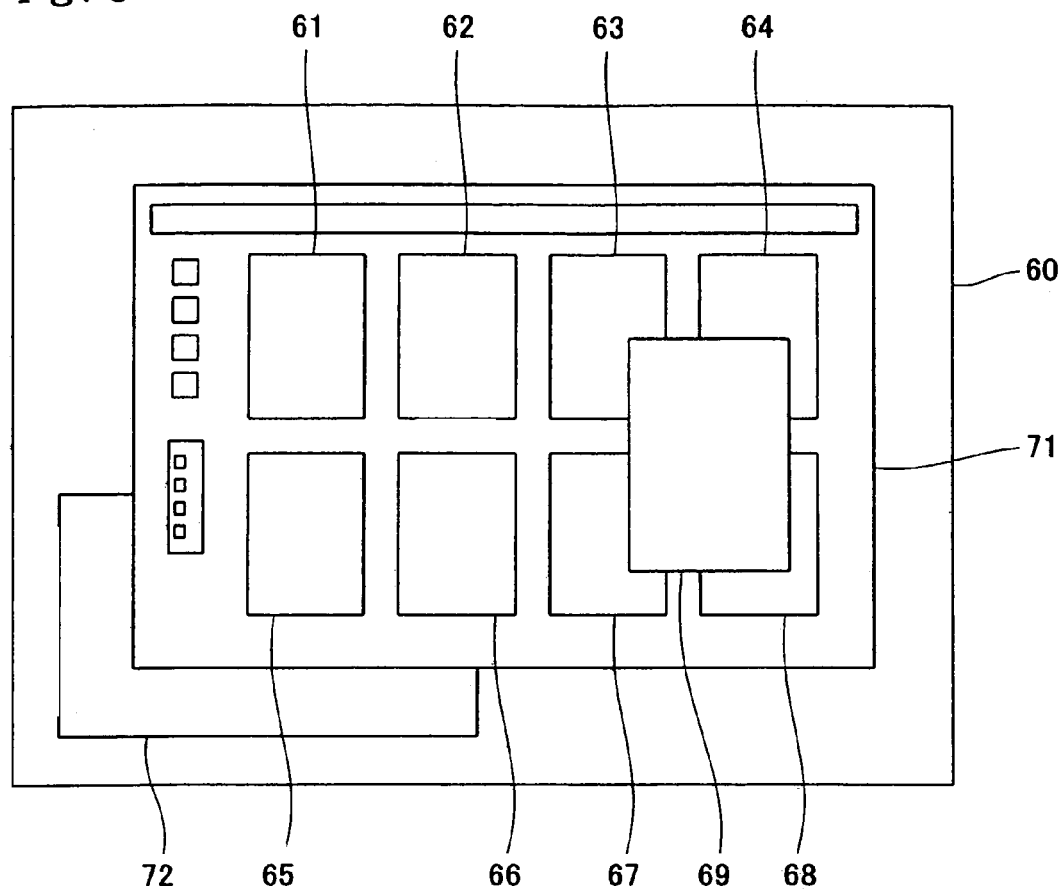
FIG. 3 is a diagram of a display region of a display device.

FIG. 3 shows a display region 60 of the display device 22b. On the display region 60, a window 71 associated with the application program E and a window 72 associated with another application program F are displayed. The same window as the window 71 of the display device 22b is displayed on each of display devices coupled to the computers other than the computer 22.

The window 71 has receiver regions 61 to 68 that display the information from the receivers 11 to 18 and a character string region 69 that displays character strings.

Figure 4:
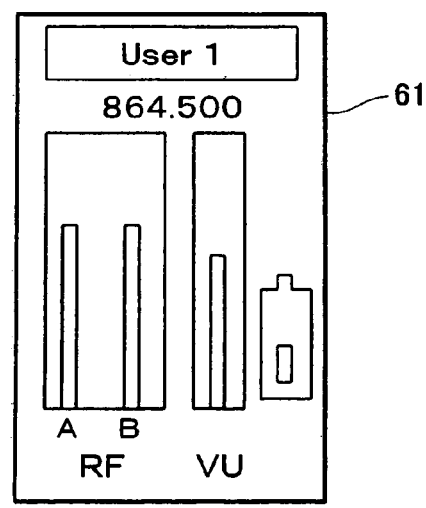
FIG. 4 is a diagram of a receiver region.

FIG. 4 shows the receiver region 61. The information from the receiver 11 is displayed on the receiver region 61. The RF level is displayed on the receiver region 61. The RF level is displayed as "A" and "B". This is because the radio wave from the wireless microphone is received in diversity format. That is, the RF levels regarding antenna A and antenna B are separately displayed.

The battery power is displayed on a right lower region of the receiver region 61. The battery power means the battery power of the wireless microphone corresponding to the receiver 11.

The VU level is displayed on the receiver region 61.

"User 1" displayed on the display region 61 is a number by which the receiver (or the corresponding wireless microphone) is identified.

A desired name may be set as this number by the user.

"864.500" displayed on the receiver region 61 indicates a frequency of the radio wave used by the receiver (or corresponding wireless microphone) by "MHz."

Likewise, the RF level, the battery power, the VU level, the number by which the receiver (or corresponding wireless microphone) is identified, and the frequency are displayed on each of the receiver regions 62 to 68 other than the receiver region 61.

Figure 5:
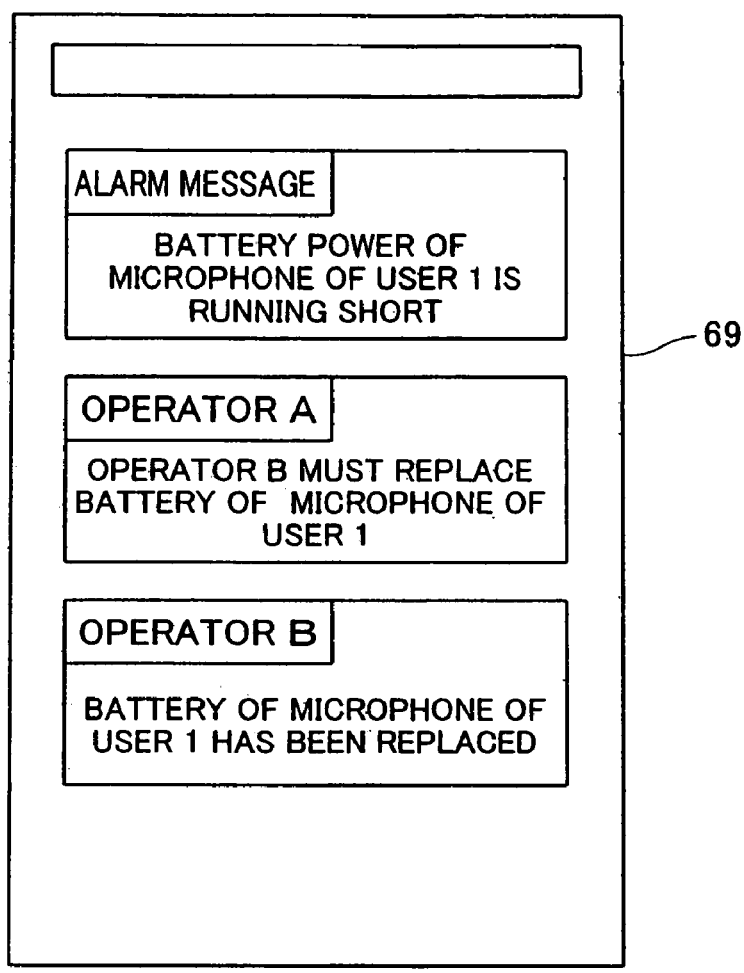
FIG. 5 is a diagram of a character string region.

FIG. 5 shows the character string region 69 on the window 71. On the character string region 69, an alarm message, a character string entered from the keyboard 24a by the operator A, and a character string entered from the keyboard 22a by the operator B are displayed.

These character strings are displayed in the following order. First, the computers 21 to 24 recognize the states of the batteries (battery powers) of the wireless microphones corresponding to the receives 11 to 18 through the LAN. When the computer (application program E) recognizes that the battery power is a predetermined threshold or less, the character string region 69 containing the alarm message is displayed on the window 71. As the alarm message, a message stating that "BATTERY POWER OF THE MICROPHONE OF USER 1 IS RUNNING SHORT" is displayed on the character string region 69.

The operator A near the computer 24 reads the alarm message displayed on the display device 24b, and enters a character string "THE OPERATOR B MUST REPLACE THE BATTERY OF THE MICROPHONE OF THE USER 1" from the key board 24a in order to instruct the operator B to replace the battery. So, this character string is displayed on the character string region 69 of the display device 24b. This character string is communicated to the computers 21 to 23 through the LAN, and is displayed on the character string region 69 of the display device of each of the computers 21 to 23.

Since the character string is displayed on the character string region 69 of the display device 22b, the operator B recognizes the instruction for replacing the battery from the operator A. In accordance with the instruction of this character string, the operator B replaces the battery of the microphone of the User 1. Then, the operator B enters a character string "THE BATTERY OF THE MICROPHONE OF THE USER 1 HAS BEEN REPLACED" from the keyboard 22a. So, this character string is displayed on the character string region 69 of the display device 22b. This character string is communicated to the computers 21, 23, and 24 through the LAN, and is displayed on the character string region 69 of the display device of each of the computers 21, 23, and 24.

The operator A reads this character string on the display device 24b, and confirms that the operator B has replaced the battery as instructed by the operator A.

In the manner described above, the same content is displayed on the display device 22b and the display device 24b. Thus, the operator A and the operator B are able to share information indicating the state of the wireless microphone communication system 1.

Thus, the same application program E runs on the respective computers 21 to 24. The computers 21 to 24 receive the information from the receivers 11 to 18 and the character string information from the computers 22 and 24 through the LAN. Therefore, the same content is displayed on the display devices coupled to the computers 21 to 24.

If a computer is installed at a location remote from the receivers 11 to 18, the operators are able to recognize the states of the receivers 11 to 18 by that computer so long as that computer is coupled to the receivers 11 to 18 through the LAN.

As mentioned above, the wireless microphone communication system 1 comprises the television camera 30 which is coupled onto the LAN. Image information from the television camera 30 may be displayed on the display devices 22b and 24b along with the information from the receivers 11 to 28. Alternatively, the image information from the television camera 30 may be stored in storage portions of the computers 22 and 24. In a further alternative, the image information from the television camera 30 and information based on the information from the receivers 11 to 18 may be stored in the storage portions of the computers 22 and 24.

The alarm message includes various messages in addition to the battery power. For example, if the RF level continues to be a predetermined value or less for a predetermined time period or more, then an alarm message stating this may be displayed. That is, it is necessary to display an alarm message stating abnormality or failure of the wireless microphone communication system 1, upon detecting them.

While each operator enters the character string from the key board to communicate with another operator, he/she may select a desired message from messages prepared in advance to display the desired message on the character string region 69.

In addition to the character strings which are entered or selected, some information entered with respect to a computer by an operator may be displayed on display devices coupled to another computers as well as a display device coupled to that computer. This makes it possible that plural operators share that information. As a result, the operators are able to communicate with each other correctly. For example, a marking or the like made on a display region of a display device by an operator may be displayed on display devices of all computers.

The character string region on which the alarm message or the character string entered by the operator are displayed may appear on the display device 22b as being associated with a receiver region (or transmitter region) on which an abnormal state of a receiver in which abnormality has occurred (or the corresponding transmitter) is displayed.

For example, the plural receiver regions may have different colors. By the color of the receiver region corresponding to the receiver associated with the information of the character string, the character string region 69 of this character string may be displayed on the display device 22. To be specific, in FIG. 3, assuming that the receiver regions 61 to 68 have different colors, the color of the receiver region 61 is blue, and information of the character string of the character string region 69 indicates abnormality of the receiver 11, the character string region 69 may be represented by blue on the display device 22b.

Furthermore, the character string region 69 on which the alarm message or the character string entered by the operator are displayed may be configured to appear near the receiver region (or transmitter region) on which the abnormal state of the receiver in which abnormality has occurred (or the corresponding transmitter) is displayed. For example, the character string region on which the alarm message or the character string entered by the operator are displayed may be configured to appear near the receiver region (or transmitter region) on which the abnormal state of the receiver in which abnormality has occurred is displayed, by pop up display. With such a configuration, each operator is able to recognize the abnormal state of the receiver directly.

The receiver region (or the transmitter region) on which the abnormal state of the receiver in which abnormality has occurred (or the corresponding transmitter) is displayed may be displayed in a display configuration different from those of receiver regions (or transmitter regions) of another receivers, for example, with a different color. Furthermore, the messages may be displayed by different colors according to the kind. This makes it easy that the operator visually checks the message. Furthermore, a destination to which a message is directed may be selected. By selecting a particular destination and sending the message to it, conflict of the message is avoided.

Subsequently, a method of detecting a dead point on the stage by the wireless microphone communication system 1 will be described.

Figure 6:
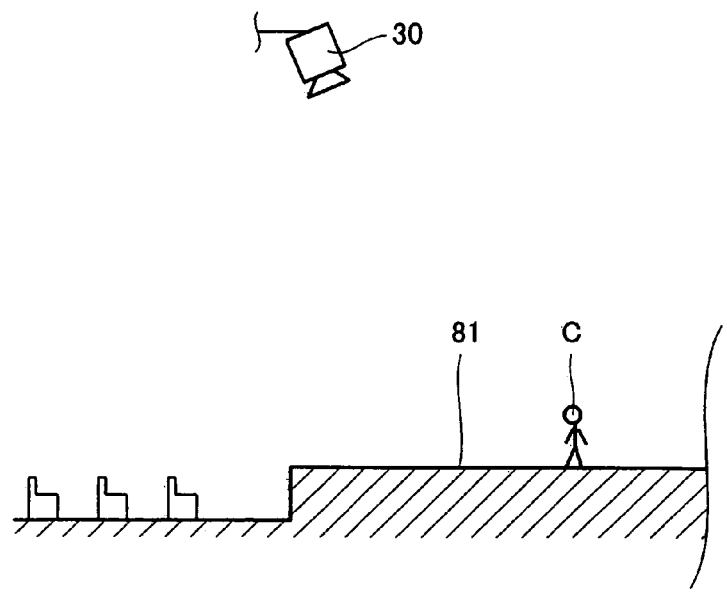
FIG. 6 is a longitudinal sectional view of a stage on which a television camera is installed.

FIG. 6 is a longitudinal sectional view of a stage 81 on which the television camera 30 is installed. As described previously, the wireless microphone communication system 1 is equipped with the television camera 30. The television camera 30 is installed above the stage 81 to take an image of the entire stage 81 from above. FIG. 6 illustrates an operator C on the stage 81. The operator C carries a wireless microphone.

Figure 7:
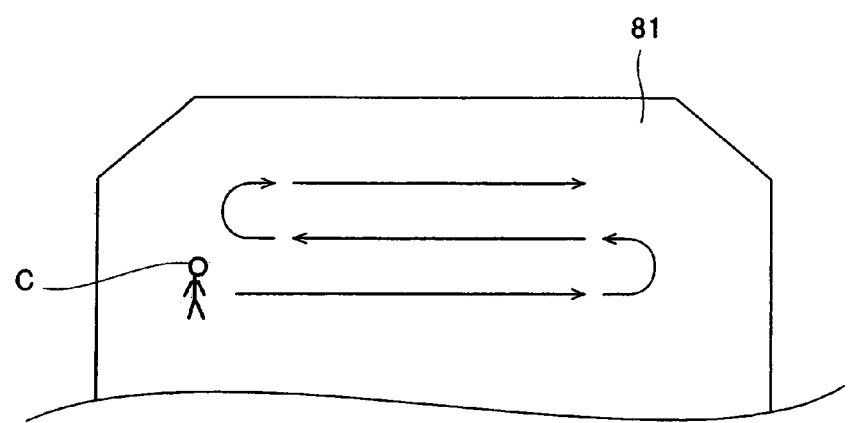
FIG. 7 is a plan view of the stage.

FIG. 7 is a plan view of the stage 81. The operator C appears on the stage 81. The operator C moves along a path indicated by an arrow in FIG. 7. In this way, the operator C walks around on the stage 81.

A radio wave from the wireless microphone carried by the operator C is received by the corresponding receiver. From this receiver, information regarding the RF level is sent to the computer 21 through the LAN.

Figure 8:
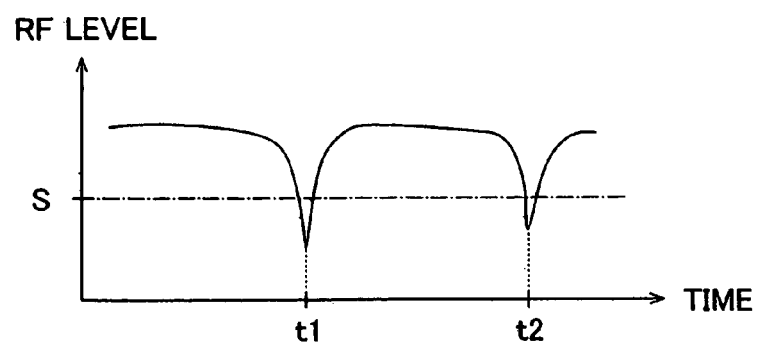
FIG. 8 is a view showing a RF level that varies with time.

FIG. 8 is a view showing the RF level that varies with time. The computer 21 continuously receives the information of the RF level on a time axis and determines whether or not the RF level is not higher than a predetermined level (threshold level). In FIG. 8, "S" indicates the predetermined level (threshold level). Turning to FIG. 8, the RF level is not higher than the level S at time t1 and time t2. The diagram illustrated in FIG. 8 may be displayed on the display device coupled to the computer 21.

The computer 21 receives the information of the RF level and image information from the television camera 30. When determining that the RF level is not higher than the predetermined level (threshold level), the computer 21 stores the image information at that time in a storage means.

Figure 9:
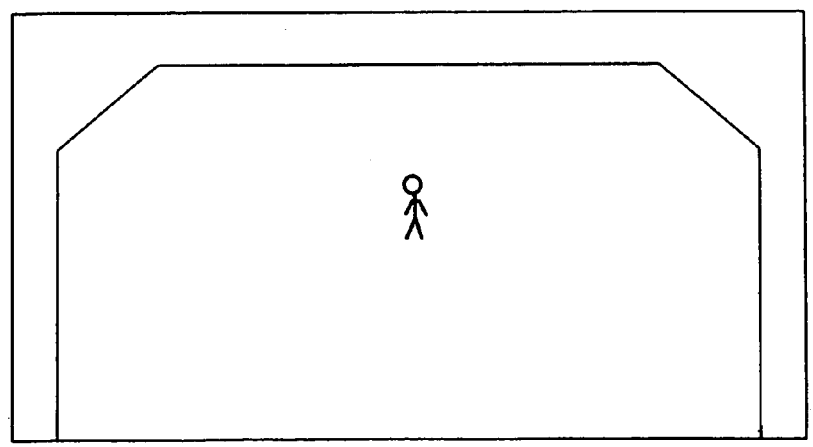
FIG. 9 is a view showing an image at time t1 which the computer receives from the television camera.

FIG. 9 illustrates an image at time t1 which is received by the computer 21 from the television camera 30. Since the RF level is not higher than the predetermined level (threshold level) at time t1, the image (image in FIG. 9) is stored in the storage means. Likewise, an image at time t2 is stored in the storage means.

It is highly probable that, when the RF level is not higher than the predetermined level, a position of the operator C at that point of time is a dead point of the wireless microphone. By checking the stored images later, the position of the dead point on the stage is recognized.

In accordance with the detection method of the dead point, the dead point is accurately detected only by one operator.

In this embodiment, an operation portion of the computer 21 functions as a control means and a memory of the computer 21 functions as the storage means. The operation portion of the computer 21 which is the control means determines whether or not the RF level is not higher than the predetermined level, and when determining that the detected RF level is not higher than the predetermined level, the image information from the television camera 30 at that point of time is stored in the memory of the computer 21 which is the storage means.

The computer 21 includes a time measuring means. Time information from the time measuring means may be stored in the memory together with the image information from the television camera 30.

In the above illustrated example, the television camera 30 is coupled to the computer 21. Alternatively, the television camera 30 may have a communication function. In that case, the television camera 30 may be directly coupled to the LAN without the computer 21.

Figure 10:
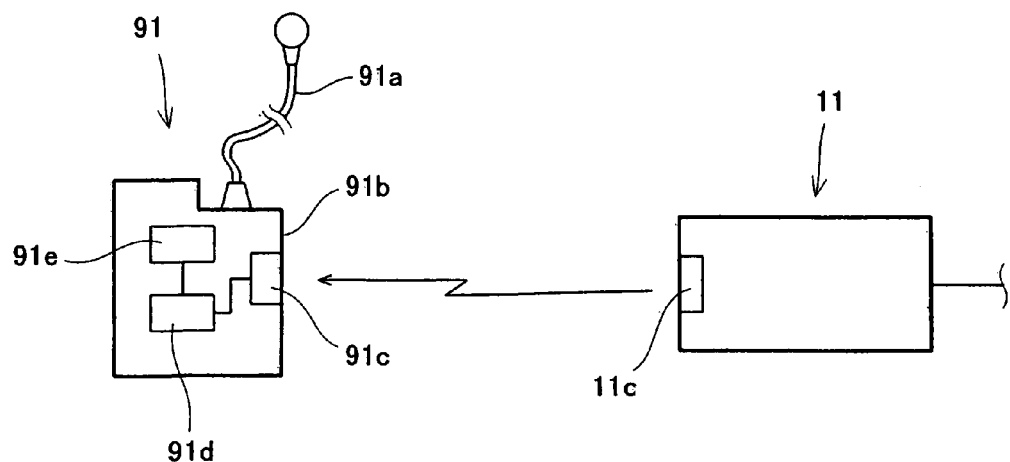
FIG. 10 is a block diagram schematically showing a configuration of a wireless microphone and a receiver.

FIG. 10 is a block diagram schematically showing a configuration of the wireless microphone 91 and the receiver 11. The wireless microphone 91 corresponds to the receiver 11. A radio wave from the wireless microphone 91 is received by the receiver 11. The wireless microphone 91 is a lavaliere type wireless microphone and includes a sound receiving portion 91a and a transmitter 91b. The transmitter 91b of the wireless microphone 91 includes an infrared interface 91c, a control portion 91d, a function control portion 91e, and a storage portion (not shown). The function control portion 91e serves to control respective functions of the wireless microphone 91, for example, a frequency and a gain of the wireless microphone 91. Various information regarding setting conditions of the wireless microphone 91 are stored in the storage portion.

The wireless microphone 91 has the infrared interface 91c. The receiver 11 corresponding to the wireless microphone 91 has an infrared interface 11c. Information is output from the infrared interface 11c of the receiver 11 in the form of an infrared signal. This information is information that has been directed from any one of the computers 21 to 24 to the receiver 11. The information from the infrared interface 11c of the receiver 11 is received by the infrared interface 91c of the wireless microphone 91. This information is sent to the control portion 91d, which controls the function control portion 91e according to this information. The transmitter 91b performs various operations according to the information from the infrared interface 11c of the receiver 11. Information is output from the infrared interface 91c of the wireless microphone 91 in the form of the infrared signal and is received by the infrared interface 11c of the receiver 11. That is, the transmitter 91b of the wireless microphone 91 and the receiver 11 have a function to transmit the information in the form of the infrared signal and a function to receive the information in the form of the infrared signal. The infrared signal is used to transmit the information, and does not interfere with the radio wave of the wireless microphone 91. In other words, this signal (infrared signal) does not negatively affect the sound signal of the wireless microphone 91 as a noise.

As described above, the transmitter 91b performs various operations according to the type of the information from the infrared interface 11c of the receiver 11. Hereinafter, various information from the infrared interface 11c of the receiver 11 and how the transmitter 91b operates according to this information will be described. The transmitter 91b performs various operations under the condition in which the control portion 91d controls the function control portion 91e.

The information from the infrared interface 11c of the receiver 11 includes command information, attribute information, and reply request information.

When the information from the infrared interface 11c of the receiver 11 is the command information, the transmitter 91b controls the function of the wireless microphone 91 according to the command information, upon receiving the command information. The command information includes various information.

When the command information is information regarding an amplitude frequency characteristic of a sound signal, the transmitter 91b controls the amplitude frequency characteristic of the sound signal according to the command information, upon receiving the command information. Thereby, quality of the sound signal which is output from the wireless microphone 91 is controlled.

When the command information is information regarding a gain of the sound signal of the transmitter 91b, the transmitter 91b controls the gain given to the sound signal according to the command signal, upon receiving the command information. Thereby, the level of the sound signal which is output from the wireless microphone 91 is controlled.

When the command information is information regarding a frequency of a carrier wave of the transmitter 91b, the transmitter 91b controls the frequency of the carrier wave according to the command information, upon receiving the command information. That is, the frequency of the radio wave from the wireless microphone 91 is changed.

When the command information is information regarding an output level of the carrier wave of the transmitter 91b, the transmitter 91b controls the output level of the carrier wave according to the command information, upon receiving the command information. The radio wave with a higher output level is sent to a remote place.

When the command information is information regarding whether or not to change the setting conditions of the transmitter 91b, the transmitter 91b enables or disables the setting conditions to be changed by the operation portion of the transmitter 91b according to the command information, upon receiving the command information. That is, the user of the wireless microphone 91 is allowed or not allowed to operate the operation portion to change the setting conditions of the wireless microphone 91. The user of the wireless microphone 91 is disabled to change the setting conditions in order to inhibit the user from erroneously operating the wireless microphone 91.

When the command information is information regarding deviation of the transmitter 91b, the transmitter 91b controls deviation according to the command information, upon receiving the command information. The deviation refers to a frequency bias of a modulated wave.

When the command information is information regarding a pilot tone of the transmitter 91b, the transmitter 91b starts or stops transmission of the pilot tone according to the command information, upon receiving the command information. The pilot tone refers to a signal used to establish symbol synchronization.

When the command information is information regarding the display of the transmitter 91b, the transmitter 91b causes the display to be turned to an operating state or a non-operating state according to the command information, upon receiving the command information. The transmitter 91b is equipped with the display which displays the setting conditions of the transmitter 91b. The term "the display is turned to the operating state" means that the display is turned to ON-state. The term "the display is turned to the non-operating state" means that the display is turned to OFF-state.

When the command information is information regarding a compander of the transmitter 91b, the transmitter 91b controls a characteristic of the compander according to the command information, upon receiving the command information. That is, the transmitter 91b controls a configuration of the compander. The compander is a device that expands and compresses the sound signal. The compander is used to enlarge a dynamic range and reduce a noise.

When the command information is information regarding a mute function of the transmitter 91b, the transmitter 91b causes the mute function to be turned to the operating state or the non-operating state according to the command information, upon receiving the command information. The term "mute function" refers to a function to mute the sound signal.

When the information from the infrared interface 11c of the receiver 11 is attribute information of the transmitter 91b, the transmitter 91b writes the attribute information in an internal storage portion, upon receiving the attribute information. The attribute information includes various information.

When the attribute information is information regarding the type of the battery to be used by the transmitter 91b, the transmitter 91b writes the type according to the received attribute information in the internal storage portion. Thus, the transmitter 91b is able to recognize the type of the battery built in the wireless microphone 91. The reason why the transmitter 91b is informed of the type of the battery is that the relationship between the battery voltage and the battery power varies according to the type of the battery. The remaining operating time of the wireless microphone is determined chiefly by the battery power of the battery. The transmitter 91b measures the battery voltage and displays the remaining operating time of the wireless microphone 91 on the display.

The transmitter 91b is caused to recognize the type of the battery in order to display the correct operating time.

When the attribute information is information regarding a number or a name assigned to the transmitter 91b, the transmitter 91b writes the number or the name according to the received attribute information in the internal storage portion. Thereby, the transmitter 91b is able to recognize the number or the name assigned to the transmitter 91b and to display the number or the name on the display. The user of the wireless microphone 91 is able to recognize the number or the name assigned to the transmitter 91b of the wireless microphone 91b used by the user according to the content displayed on the display.

The infrared interface 91c of the wireless microphone 91 and the infrared interface 11c of the receiver 11 have a two-way communication function. The transmitter 91b sends reply information to the receiver 11 in order to inform the receiver 11 that the wireless microphone 91 has received the signal or the transmitter 91b performed control correctly according to the information from the receiver 11. In this manner, correct communication is carried out.

The reply information is output from the infrared interface 91c of the transmitter 91b of the wireless microphone 91 when a signal of the reply request information is output from the infrared interface 11c of the receiver 11.

When the signal of the reply request information is output from the interface 11c of the receiver 11 and the transmitter 91b receives the reply request information, the transmitter 91b sends the reply information to the receiver 11 in the form of the infrared signal according to the reply request information.

The reply request information includes various information. For example, when the reply request information is information to request the transmitter 91b to send the setting conditions of the transmitter 91b to the receiver 11, the transmitter 91b sends information regarding the setting conditions as the reply information according to the reply request information, upon receiving the reply request information. The information regarding the setting conditions includes an amplitude frequency characteristic of the sound signal of the transmitter 91b or information regarding the gain given to the sound signal of the transmitter 91b. These information are stored in the storage portion of the transmitter 91b of the wireless microphone 91. When the information of all the setting conditions of the transmitter 91b have been sent to the receiver 11, another transmitters may be configured to change setting conditions into those identical to the setting conditions of the transmitter 91b.

Figure 11:
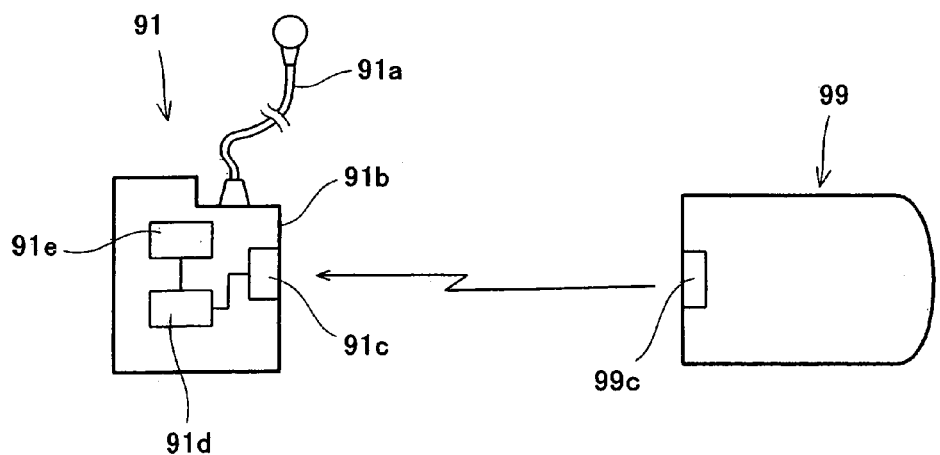
FIG. 11 is a block diagram schematically showing a configuration of the wireless microphone and a personal digital assistance (PDA)

FIG. 11 is a block diagram schematically showing a configuration of the wireless microphone 91 and a personal digital assistant (PDA) 99. As described previously, the function of the wireless microphone 9 is controlled according to the information in the form of the infrared signal. This information need not be output from the receiver 11. For example, this information may be output from the personal digital assistant (PDA) 99. The personal digital assistance (PDA) 99 in FIG. 11 includes an infrared interface 99c from which the information is output in the form of the infrared signal. This information is received by the infrared interface 91c of the wireless microphone 91 and thereby the frequency characteristic, the gain and so on of the sound signal of the wireless microphone 91 are controlled.

In a case where plural performers respectively carry wireless microphones, the operator carrying the PDA 99 is able to control functions of the respective wireless microphones of the performers. The use of the PDA 99 advantageously makes it easy to control the functions.

As described previously, the infrared interface 91c of the wireless microphone 91 and the infrared interface 11c of the receiver 11 have a two-way communication function. In this embodiment, since the infrared interface 99c of the PDA 99 has a two-way communication function, two-way communication is able to be made between the wireless microphone 91 and the PDA 99. Therefore, by sending the reply information from the wireless microphone 91 to the PDA 99, the PDA 99 is informed that the wireless microphone 91 has received the infrared signal from the PDA 99 or the wireless microphone 91 has been controlled correctly according to the information from the PDA 99.

Alternatively, communication may be performed between the receiver 11 and the PDA 99. With this configuration, the information of the setting conditions of the transmitter 91b may be sent from the receiver 11 to the PDA 99, and further from the PDA 99 to wireless microphone 91 (transmitter). To be specific, first, the receiver 11 performs infrared communication with the PDA 99 as if the receiver 11 performed infrared communication with the transmitter 91b of the wireless microphone 91. Thereby, the command information or the attribute information is output from the receiver 11 to the PDA 99, which stores these information in the internal storage portion. Then, the PDA 99 sends the information stored in the storage portion to the transmitter 91b of the wireless microphone 91. The wireless microphone 91 changes the setting conditions or stores the received attribute information in the internal storage portion as if the wireless microphone 91 received these information from the receiver 11.

When the receiver 11 sends to the PDA 99, reply request information to request the PDA 99 to inform the receiver 11 of the setting conditions of the wireless microphone 91, the PDA 99 sends to the receiver 11, the information regarding the setting conditions of the wireless microphone 91 that is stored in the internal storage portion, as reply information.

When the PDA 99 sends the reply request information to the transmitter 91b of the wireless microphone 91, the transmitter 91b of the wireless microphone 91 sends the reply information to the PDA 99, in response to the reply request information. Based on the reply information, the PDA 99 is able to recognize the setting conditions of the wireless microphone 91, for example, the gain of the sound signal of the wireless microphone 91. Based on this information, the PDA 99 may send to a transmitter of another wireless microphone, for example, command information to change the setting conditions of the transmitter of another wireless microphone.

In a further alternative, the information regarding the wireless microphone may be communicated between two PDAs by infrared communication. In other words, one of the two PDAs acts as the transmitter of the wireless microphone and the other acts as the receiver. Thereby, information regarding the wireless microphone is communicated between the two PDAs.

As described previously, when the information of all setting conditions regarding one transmitter are sent to the receiver 11, another transmitter is able to change the setting conditions into those identical to the setting conditions of the one transmitter. In the configuration in which communication is performed between the receiver 11 and the PDA 99, one transmitter and another transmitter are configured to have the same setting conditions by an operation performed as follows. First, the receiver 11 sends to the corresponding transmitter (first transmitter), reply request information regarding the setting conditions of the transmitter. The transmitter (first transmitter) sends to the receiver 11, the information regarding the setting conditions. Then, the receiver 11 communicates the information of the setting conditions of the transmitter (first transmitter) to the PDA 99. Then, the PDA sends command information to another transmitter (second transmitter) so that the setting conditions of the transmitter (second transmitter) become identical to those of the transmitter (first transmitter).

By using a dedicated remote controller or a general-purpose remote controller as the PDA, the wireless microphone communication system becomes inexpensive.

Figure 12:
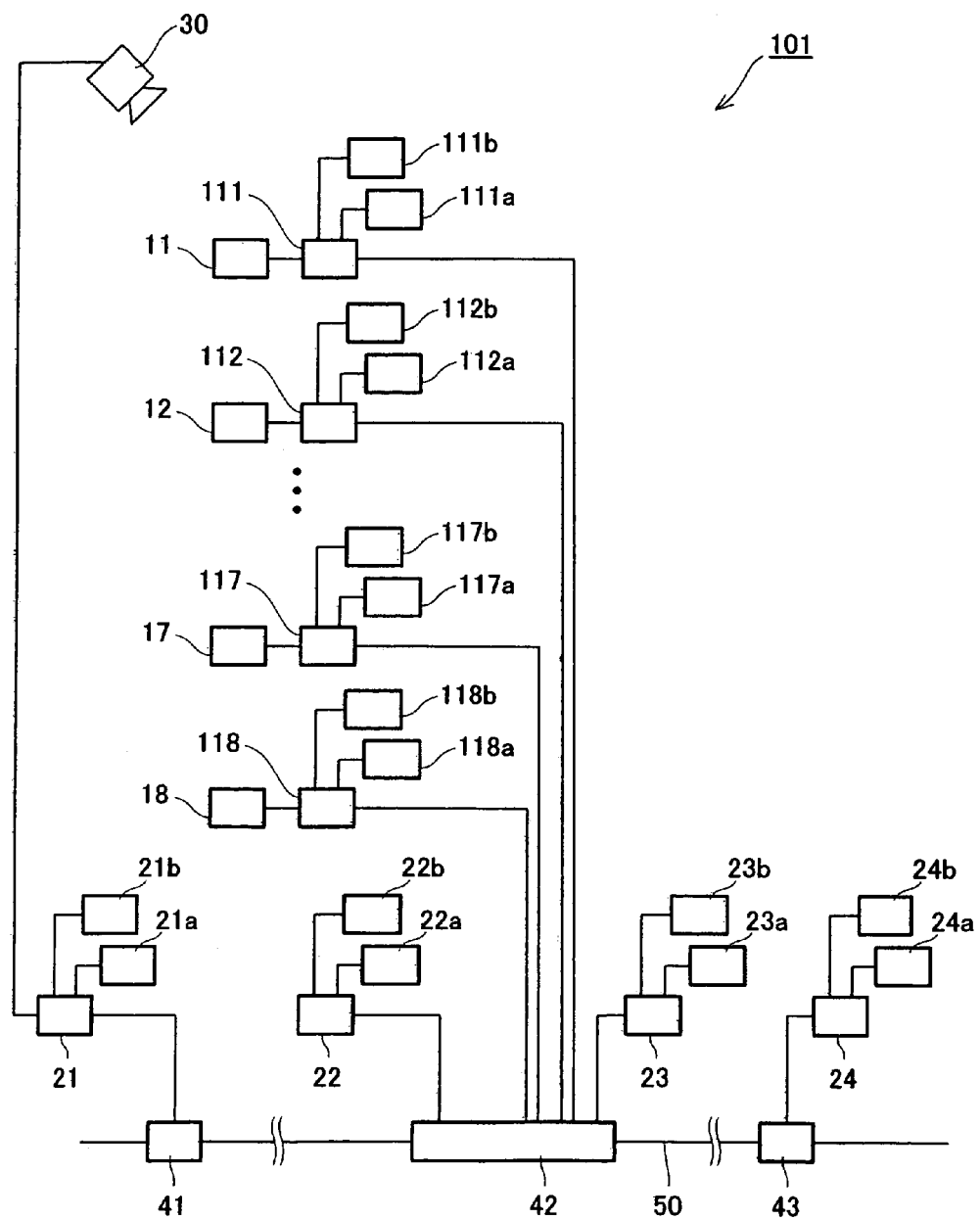
FIG. 12 is a block diagram of a wireless microphone communication system.

Subsequently, a wireless microphone communication system in which receivers that receive radio waves from transmitters of wireless microphones are coupled to LAN through controllers having LAN interfaces will be described. FIG. 12 is a view schematically showing a configuration of a wireless microphone communication system 101.

The wireless microphone communication system 101 includes the computers 21, 22, 23, and 24 as in the wireless microphone communication system 1 of FIG. 1. The computers 21, 22, 23, and 24 in FIG. 12 have functions identical to those of the computers 21, 22, 23, and 24 of FIG. 1.

The wireless microphone communication system 101 is different from the wireless microphone communication system 1 of FIG. 1 as follows. In the wireless microphone communication system 1 of FIG. 1, the receivers 11 to 18 have the LAN interfaces and are coupled to the HUB 42 through the LAN interfaces rather than the controllers 21 to 24, while in the wireless microphone communication system 101 in FIG. 12, the receivers 11 to 18 are coupled to the HUB 42 through the controllers 111 to 118 having the LAN interfaces. The controllers 111 to 118 may be configured by computers.

As in the computers 21 to 24, key boards 111a to 118a which are input devices and display devices 111b to 118b are coupled to the controllers 111 to 118.

Each of the controllers 111 to 118 receives information from another controller to which the corresponding receiver is coupled. The information from the controller includes, the RF level (receiving field intensity), the audio output level (VU level), and so on. The wireless microphone corresponding to each receiver sends, to the receiver, information of the battery power of the wireless microphone. Each of the controllers 111 to 118 receives the information of the battery power from another controller. These information are displayed on the display devices 111b to 118b. That is, the respective controllers 111 to 118 have functions identical to those of the computers 21 to 24.

The controllers 111 to 118 in the wireless microphone communication system 101 of FIG. 12 are operated by an operator.

The controllers 111 to 118 in the wireless microphone communication system 101 of FIG. 12 enable plural operators to equally recognize the state of the communication system using the wireless microphones.

Subsequently, another wireless microphone communication system in which the receivers that receive the radio wave from the transmitters of wireless microphones are coupled to the LAN through the controllers having the LAN interfaces will be described.

FIG. 12 shows the wireless microphone communication system 101 in which the controllers 111 to 118 to which the receivers 11 to 18 that receive the radio wave from the transmitters of the wireless microphones are coupled, through the LANs, to the controllers 21, 22, 23, and 24 to which the receivers are not coupled.

The controllers (computers) 21, 22, 23, and 24 to which the receivers are not coupled and the corresponding peripheral devices 21a, 21b, 22a, 22b, 23a, 23b, 24a, and 24b may be omitted from the wireless microphone communication system 101 of FIG. 12. This results in a wireless microphone communication system in which the plurality of (eight) controllers (computers) 111 to 118 to which the receivers 11 to 18 that receive the radio wave from the transmitters of the wireless microphones are coupled to each other through the LAN. While eight controllers (computers) 111 to 118 are coupled to the common HUB 42 in FIG. 12, the respective controllers (computers) 111 to 118 may alternatively be equipped with HUBs which are coupled to the Ethernet 50. In a case where the plurality of controllers (computers) 111 to 118 are installed to be distant from each other, they may be operated by the associated operators. These operators are able to equally recognize the state of the communication system using the wireless microphones.

Numerous modifications and alternative embodiments of the invention will be apparent to those skilled in the art in view of the foregoing description. Accordingly, the description is to be construed as illustrative only, and is provided for the purpose of teaching those skilled in the art the best mode of carrying out the invention. The details of the structure and/or function may be varied substantially without departing from the spirit of the invention and all modifications which come within the scope of the appended claims are reserved.

INDUSTRIAL APPLICABILITY

In accordance with the present invention, plural operators are able to equally recognize a condition of a communication system using wireless microphones and to change settings and the like quickly. Therefore, the present invention is applicable to fields of wireless microphone communication systems.

The invention claimed is:

1. A wireless microphone communication system for use by a plurality of operators on a stage, comprising:
    a plurality of wireless microphones each independently portable on the stage by the operators;
    a wireless receiver operable to wirelessly receive radio signals from each of the plurality of wireless microphones; and
    a plurality of computers each being connected to the wireless receiver over a Local Area Network (LAN) different from the radio signals received by the wireless receiver and each being connected to a respective display and a respective keyboard;
    wherein the wireless receiver obtains from the radio signals and continuously sends over the LAN information indicative of a status of at least one of the plurality of wireless microphones,
    wherein the status comprises at least one of: an RF level, a VU level, and a battery level,
    wherein the plurality of computers continuously receives the information sent over the LAN from the wireless receiver,
    wherein each computer displays the received information,
    wherein each computer displays one or more character strings input through the respective keyboard by an operator associated with the computer, and sends the one or more character strings to the other computers, and
    wherein each computer also displays one or more character strings being input by other operators associated with other computers through respective keyboards connected to the other computers and being sent from the other computers, thereby allowing all of the displays to display the same content.

2. A wireless microphone communication system of claim 1, wherein each computer further displays a marking made by an operator on a display region, and sends the marking to the other computers, and wherein each computer further displays markings being made by the other operators and being sent from the other computers.

3. A wireless microphone communication system of claim 1, further comprising:
   a camera, separated from the wireless microphones, the wireless receiver, and the computers, the camera positioned above the stage for acquiring images of the entire stage while a given wireless microphone is carried and moved by an operator on the stage, the camera being connected over the LAN to a given computer; and
   wherein the given computer continuously receives from the camera the images acquired by the camera;
   wherein the given computer continuously determines whether or not the information indicative of the status of the given wireless microphone indicates an RF level lower than a predetermined threshold; and
   wherein the given computer stores an image received at a time when the given computer determines that the RF level is lower than the predetermined threshold.

4. A wireless microphone communication system for use by a plurality of operators on a stage, comprising:
   a plurality of wireless microphones each independently portable on the stage by the operators;
   a wireless receiver operable to wirelessly receive radio waves from one or more of the wireless microphones and operable to obtain information indicative of a status of the one or more wireless microphones, the status comprising at least one of: an RF level, a VU level, and a battery level; and
   a plurality of computers each being connected to the wireless receiver over a LAN separate from the wireless signals, each computer being coupled to a respective display and a respective keyboard, and each having circuitry configured to:
      receive over the LAN, from the wireless receiver, the information indicative of status of the one or more wireless microphones;
      display the received information on the respective display;
      receive first character strings input through the respective keyboard by one of the plurality of operators and display the first character strings;
      send the first character strings to other computers over the LAN; and
      receive over the LAN, from the other computers, second character strings input by others of the plurality of operators by way of keyboards coupled to other computers; and
      display the received first and second character strings together on the display.

5. A wireless microphone communication system of claim 4, the plurality of computers each having the circuitry configured further to:
   receive a first marking made by the one of the operators on the respective display, and send the first marking to other computers over the LAN;
   receive over the LAN, from the other computers, second markings made by the others of the operators on displays coupled to other computers; and
   display the first and second markings together on the respective display.

6. A wireless microphone communication system of claim 4, further comprising:
   a camera, separated from the wireless microphones, the wireless receiver, and the computers, the camera being positioned above the stage for acquiring images of the entire stage while a given wireless microphone is carried and moved by an operator on the stage, the camera being connected over the LAN to a given computer; and
   wherein the given computer has circuitry configured further to:
      continuously receive, from the camera, the images acquired by the camera;
      continuously determine whether or not the information indicative of the status of the given wireless microphone indicates an RF level lower than a predetermined threshold; and
      store an image received at a time when the given computer determines that the RF level is lower than the predetermined threshold.

* * * * *